(12) United States Patent
Erlenkeuser et al.

(10) Patent No.: US 8,151,638 B2
(45) Date of Patent: Apr. 10, 2012

(54) SPRING FORCE COMPONENT TESTER

(75) Inventors: Heiko F. Erlenkeuser, Anderson, SC (US); Joseph A. Nater, Greenville, SC (US)

(73) Assignee: Robert Bosch GmbH, Stuttgart (DE)

( * ) Notice: Subject to any disclaimer, the term of this patent is extended or adjusted under 35 U.S.C. 154(b) by 447 days.

(21) Appl. No.: 12/533,638

(22) Filed: Jul. 31, 2009

(65) Prior Publication Data
US 2010/0139359 A1   Jun. 10, 2010

Related U.S. Application Data

(60) Provisional application No. 61/201,161, filed on Dec. 7, 2008.

(51) Int. Cl.
  *G01L 1/04* (2006.01)
  *G01L 1/16* (2006.01)
  *G01N 3/08* (2006.01)
(52) U.S. Cl. .............. 73/161; 73/767; 73/781; 73/855; 73/862.391
(58) Field of Classification Search .............. 73/161, 73/763, 767, 781, 788, 790, 818, 855, 856, 73/860, 862.391, 862.641
See application file for complete search history.

(56) References Cited

U.S. PATENT DOCUMENTS

| | | | | |
|---|---|---|---|---|
| 1,874,780 A | * | 8/1932 | McGuckin | 73/161 |
| 2,088,372 A | * | 7/1937 | Gogan | 73/161 |
| 2,170,197 A | * | 8/1939 | Gumprich | 73/161 |
| 2,271,739 A | * | 2/1942 | Link | 73/161 |
| 2,340,277 A | * | 1/1944 | Sturtevant | 73/161 |
| 2,417,196 A | * | 3/1947 | Hartley et al. | 73/161 |
| 2,518,408 A | * | 8/1950 | Weyand | 73/818 |
| 2,568,596 A | * | 9/1951 | Ruge | 73/161 |
| 2,639,613 A | * | 5/1953 | Richmond | 73/161 |
| 2,671,210 A | * | 3/1954 | Aviles | 73/161 |

(Continued)

FOREIGN PATENT DOCUMENTS

CN        2076234        5/1991
(Continued)

OTHER PUBLICATIONS

Lietz, S., et al., "A New Six-Component Force Vector Sensor—First Investigations", IMEKO 20th TC3, 3rd TC16 and 1st TC22 International Conference, Cultivating Metrological Knowledge, Merida, Mexico, Nov. 27-30, 2007.

(Continued)

*Primary Examiner* — David Rogers
(74) *Attorney, Agent, or Firm* — Michael Best & Friedrich LLP (57) ABSTRACT

A spring force component tester for determining a load distribution on each end of a spring of generally cylindrical shape using three, mutually-parallel load cells. One tester includes a lower plate and an upper plate movable with respect to the lower plate. Each plate includes a plurality of recesses and a load cell positioned in each recess. Each plurality of recesses is positioned such that a center of each recess is a point on a circle coaxial to the plate. The tester also includes a data logger that obtains and stores load cell outputs from the load cells and spring tester electronics that obtain height measurements of the upper plate and send a trigger signal to a computer. The computer executes application software when the computer receives the trigger signal that reads the load cell outputs stored in the data logger, and calculates a spring force acting along the spring axis between approximately 0.5 Newton and 100 Newton.

27 Claims, 10 Drawing Sheets

U.S. PATENT DOCUMENTS

| | | | | |
|---|---|---|---|---|
| 2,784,588 | A | * | 3/1957 | Humble et al. ................. 73/161 |
| 2,920,482 | A | * | 1/1960 | Droke .............................. 73/161 |
| 3,165,926 | A | * | 1/1965 | Orr et al. ......................... 73/161 |
| 3,206,971 | A | | 9/1965 | Felix |
| 3,282,083 | A | * | 11/1966 | Sonderegger ................... 73/161 |
| 3,335,604 | A | * | 8/1967 | Lyell ............................... 73/161 |
| 3,531,987 | A | * | 10/1970 | Johnson .......................... 73/161 |
| 3,638,486 | A | * | 2/1972 | Lambert ......................... 73/161 |
| 3,640,129 | A | * | 2/1972 | Bandimere ................ 73/114.79 |
| 3,675,479 | A | * | 7/1972 | Carlson ........................... 73/161 |
| 3,834,228 | A | | 9/1974 | Wachholz |
| 4,056,974 | A | | 11/1977 | Klinger et al. |
| 4,086,809 | A | * | 5/1978 | Wu et al. ......................... 73/161 |
| 4,157,033 | A | * | 6/1979 | Shereda et al. ................. 73/161 |
| 4,175,431 | A | * | 11/1979 | DeTournay ..................... 73/161 |
| 4,641,521 | A | * | 2/1987 | Lawrence ....................... 73/161 |
| 5,033,298 | A | | 7/1991 | Hueck |
| 5,088,333 | A | * | 2/1992 | Kiely et al. ................ 73/862.53 |
| 5,714,695 | A | | 2/1998 | Bruns |
| 5,832,774 | A | | 11/1998 | Smith |
| 5,872,319 | A | | 2/1999 | Bruns et al. |
| 6,128,950 | A | | 10/2000 | Hoagland |
| 6,689,962 | B2 | | 2/2004 | Breed et al. |
| 7,069,778 | B1 | | 7/2006 | Strehler |
| 7,110,926 | B2 | | 9/2006 | Nishizawa et al. |
| 7,143,643 | B2 | | 12/2006 | Umebayashi |
| 7,437,943 | B2 | | 10/2008 | Munz et al. |
| 2006/0107511 | A1 | | 5/2006 | Pare |
| 2008/0184807 | A1 | * | 8/2008 | Nakano .......................... 73/818 |

FOREIGN PATENT DOCUMENTS

| | | |
|---|---|---|
| CN | 101038219 | 9/2007 |
| DE | 3720876 A1 * | 2/1988 |
| DE | 4410680 | 10/1994 |
| GB | 2199958 | 7/1988 |
| JP | 57094626 A * | 6/1982 |
| JP | 60010143 A * | 1/1985 |

OTHER PUBLICATIONS

Zwick/Roell, Compression Test on Coil Springs, Zwick Materials Testing, published as early as Dec. 17, 2007.

Link, Squareness Under Load Spring Test Unit, available online at: <http://www.linkeng.com/springtesters/SquarenessUnderLoadSpringTestUnit.htm>, published as early as Dec. 17, 2007.

Zwick/Roell, Test Fixtures for Multi-Channel Spring Testing, available online at: <http://www.zwick.com/en/products/specimen-grips-and-test-tools/test-fixtures-for-multi-channel-spring-testing.html>, published as early as Dec. 1, 2009, but, to the best of our knowledge, not before Dec. 7, 2008.

* cited by examiner

SPRING FORCE COMPONENT TESTER

RELATED APPLICATIONS

The present application claims priority to U.S. Provisional Patent Application Ser. No. 61/201,161 of the same title, filed on Dec. 7, 2008, the entire content of which is herein incorporated by reference.

FIELD OF INVENTION

Embodiments of the invention relate to three-dimensional force component testing. More specifically, embodiments of the invention relate to methods of and devices for determining force penetration points or positions and load distribution on each end of a spring.

BACKGROUND

Springs are used in numerous devices and applications. Springs are tested during research and development (and sometimes during manufacturing of end products that include the springs) to ensure that the springs satisfy their design requirements.

SUMMARY

In many cases, it is necessary to measure the load on a spring and to characterize a spring's particular attributes as the spring is acted on by a number of three-dimensional forces. Much of the spring testing equipment already available on the market addresses only squareness under load ("SUL"), and such equipment is not, at least in general, capable of measuring springs in a very low force range due to friction losses. Further, SUL testers are very application specific, while a device with general applicability may be significantly more useful.

Another deficiency of a number of currently available spring testers is that they fail to describe the effects of (or provide information regarding) all three-dimensional forces acting on a spring. Current equipment, for example, may consider only a side force or a moment in a primary direction, or such equipment may only consider springs tolerating a force range of large magnitude. In general, known testing equipment measures springs with an axial minimum force ranging from about 10 kN to about 20 kN. In other words, known testing equipment only measures springs with high minimum force ranges. Embodiments of the invention overcome at least some of the drawbacks and deficiencies of prior-art spring tester systems by providing a method and device for three-dimensional force component testing of springs with low axial minimum force ranges.

In one embodiment, the invention includes two spring test fixtures (or plate and load-cell assemblies) that attach to a standard spring tester and that have the capability of determining the load distribution on each end of a spring by using a plurality of load cells located on each of the fixtures (e.g., between two plates). The spring force tester system (with the fixtures in place) then measures penetration points at both spring ends of helical springs, wave springs, disc springs, and other types of springs of a generally-cylindrical shape.

In at least one embodiment, the invention is designed to measure forces ranging from low primary axial forces as small as 0.5N up to forces as large as 100N. Force components that are collinear with the spring axis can also be measured and calculated into vector penetration point coordinates. The spring force tester system can determine side forces and moments in a primary direction and in other directions as well.

One embodiment of the invention includes a fixture and machine parts as well as computer software that calculates force vector penetration points for each spring end based on load distribution of the load cells at each spring end. The invention also includes a method for calibrating the spring tester assembly and a method for calculating the various force vectors acting on a spring and the related moments.

In particular, one embodiment of the invention includes a system for testing a spring. The system includes a lower plate and an upper plate. The upper plate is movable with respect to the lower plate. Each plate includes a plurality of recesses and a load cell positioned in each recess. Each plurality of recesses is positioned such that a center of each recess is a point on a circle coaxial to the plate. The system also includes a data logger that obtains and stores load cell outputs from the load cells in the lower plate and the upper plate and spring tester electronics that obtain height measurements of the upper plate and send a trigger signal to a computer. The computer includes a processor and a memory module, and the memory module stores application software. The application software is executable by the processor when the computer receives the trigger signal to read the load cell outputs stored in the data logger, and calculate a spring force based on the load cell outputs, wherein the spring force is between approximately 0.5 Newton and 100 Newton.

Additional embodiments of the invention provide a method of calibrating a spring tester device. The method includes providing a lower plate and an upper plate. The upper plate is movable with respect to the lower plate. Each plate includes a plurality of recesses and a load cell positioned in each recess. Each plurality of recesses is positioned such that a center of each recess is a point on a circle coaxial to the plate. The method also includes providing a first specimen plate positioned on the lower plate and including a plurality of countersinks and providing a second specimen plate positioned on the upper plate and including a plurality of countersinks.

In addition, the method includes aligning the lower plate and the upper plate such that the first specimen plate is parallel and concentric with the second specimen plate, positioning a spring-loaded calibration device perpendicular and between the first specimen plate and the second specimen plate by positioning a first end of the calibration device in one of the plurality of countersinks in the first specimen plate and positioning a second end of the calibration device in one of the plurality of countersinks in the second specimen plate, and calculating a spring force of the spring-loaded calibration device based on load cell outputs generated by the load cells included in the lower plate and the upper plate, wherein the spring force is between approximately 0.5 Newton and 100 Newton. The method further includes using the calculated spring force, a known spring force for the spring-loaded calibration device, and positions of the plurality of countersinks in the first specimen plate and the second specimen plate to calibrate the spring tester device.

Yet other embodiments of the invention include a method of inspecting a spring. The method includes providing a lower plate and an upper plate. The upper plate is movable with respect to the lower plate. Each plate includes a plurality of recesses and a load cell positioned in each recess. Each plurality of recesses is positioned such that a center of each recess is a point on a circle coaxial to the plate. The method also includes positioning the spring perpendicular to and between the lower plate and the upper plate, determining a height of the upper plate, obtaining load cell outputs from the load cells positioned in the lower plate and the upper plate, and calculating a load center for a first end of the spring and a load center for a second end of the spring based on the load cell outputs.

Other aspects of the invention will become apparent by consideration of the detailed description and accompanying drawings.

BRIEF DESCRIPTION OF THE DRAWINGS

Corresponding reference characters indicate corresponding parts throughout the drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Figure 1:
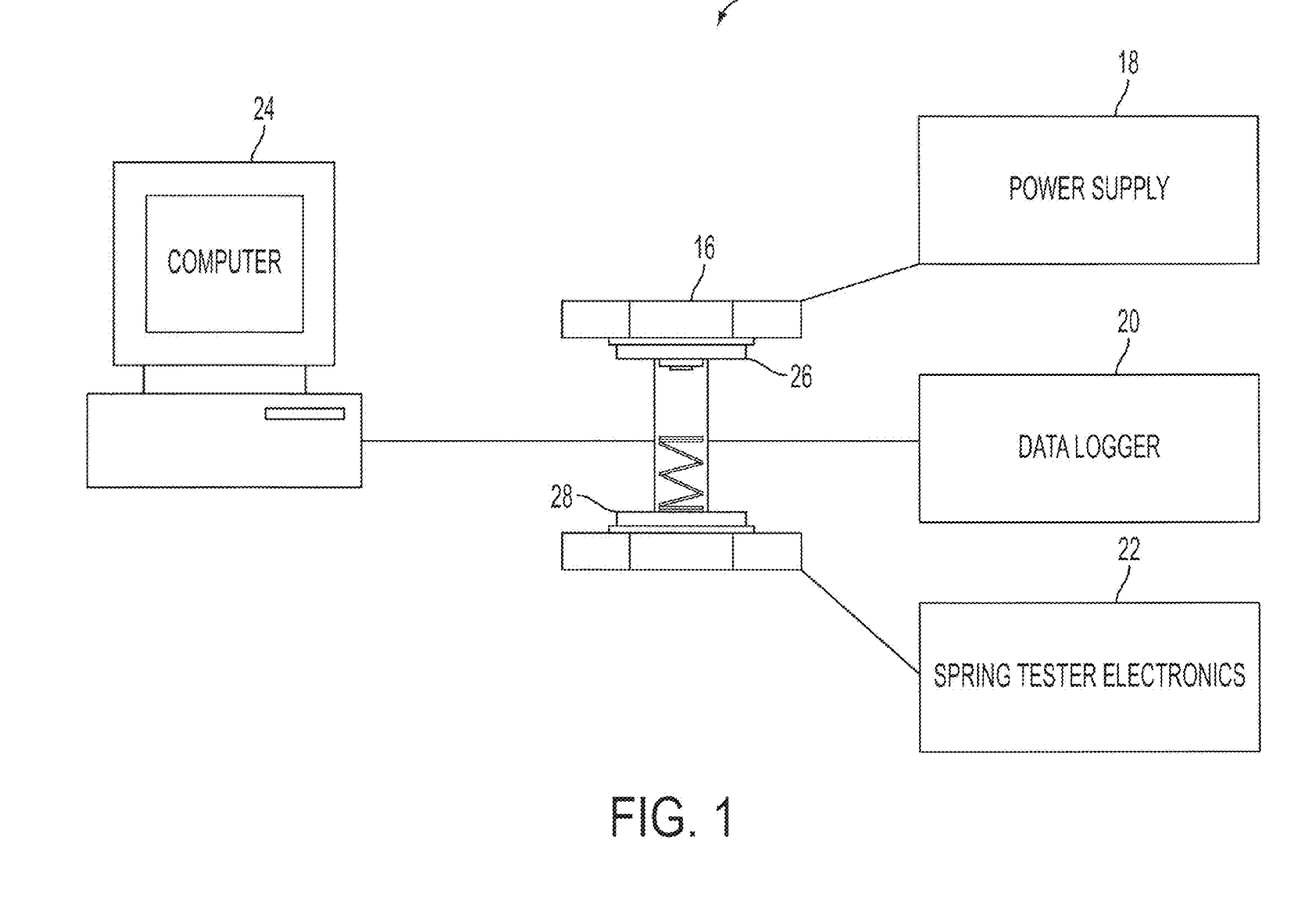
FIG. 1 illustrates, in simplified form, a spring tester system according to one embodiment of the invention.

Referring now to the drawings, a spring tester system 12 is shown in FIG. 1. In the embodiment illustrated, the spring tester system 12 includes a test fixture 16, a power supply 18, a data logger 20, and spring tester electronics 22. The spring tester system 12 also includes a computer 24.

The power supply 18 provides power to components of the system 12. In one embodiment, the power supply is a Lambda LA-200H power supply. In one embodiment, the data logger 20 is an Agilent Technologies 34970A data acquisition switch unit. The spring tester electronics 22 may be implanted using commercially available units such as a Model 3700 Display Module from Link Engineering Company. The computer 24 may be a personal computer running a Microsoft operating system.

Signals from load cells (described below) in the test fixture 16 are transmitted to or read by the data logger 20. The spring tester electronics 22 measure the height of the spring or the distance between upper and lower plates (discussed below) of the test fixture 16 based on information from a height measurement device (discussed below) in the test FIG. 16. The spring tester electronics 22 send a trigger signal (e.g., a data string containing height information) to the computer 24. In response to the trigger signal, the computer 24 reads the load cell values (voltages) stored in the data logger 20. Once the computer 24 calculates the forces from the information from the data logger, the computer generates an output such as an ASCII file or spreadsheet (e.g., an Excel spreadsheet) populated with force values. The software and the computer 24 used to calculate the forces are described in greater detail below.

The computer 24 includes a processor (not shown) such as a programmable microprocessor, memory, and input and output devices, such as a keyboard, a mouse, and a monitor (or display). As noted, an operating system is loaded in the memory and application software (described below) is loaded into memory of the computer and fetched and executed by the processor. As programmed with the application software, the computer 24 performs calculations on the data it receives from the data logger 20.

Figure 2:
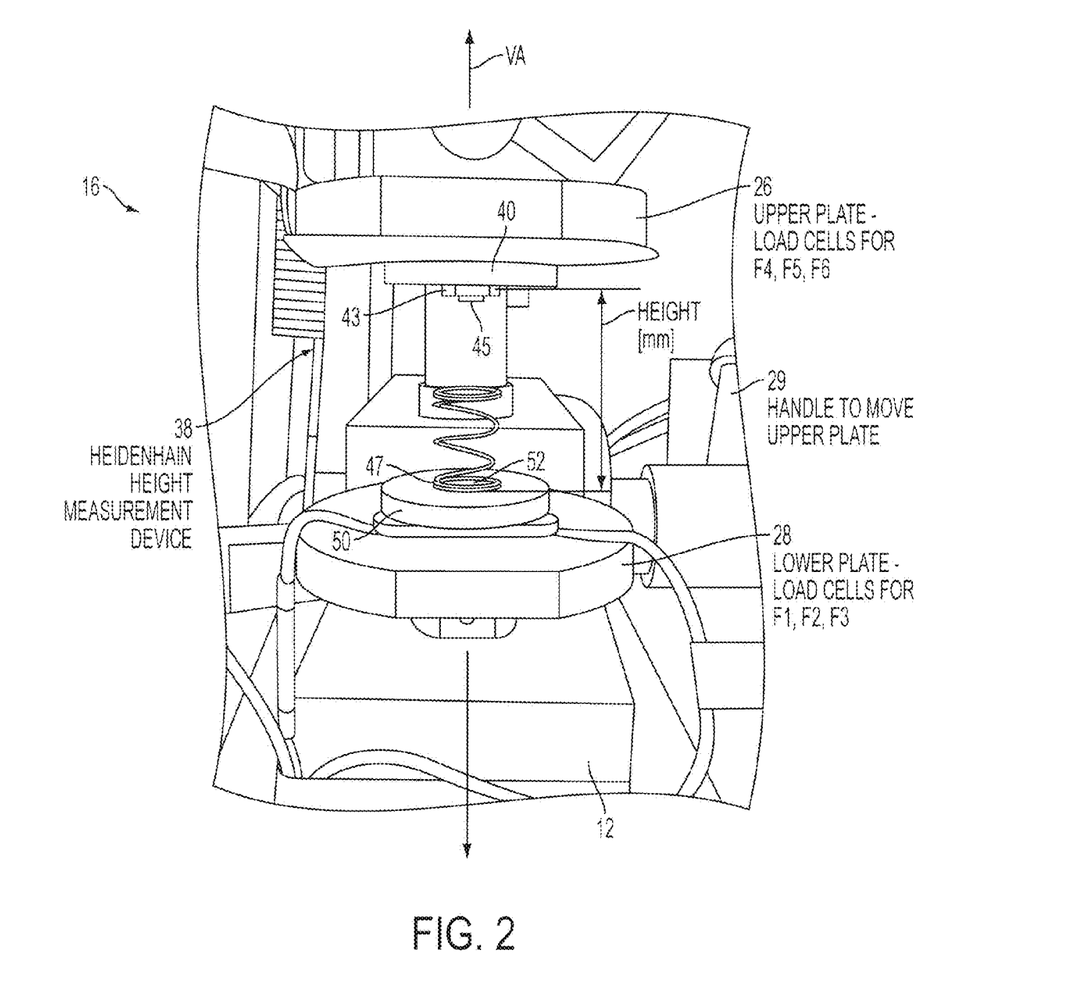
FIG. 2 is a perspective view of a spring tester constructed in accordance with embodiments of the invention.

FIG. 2 illustrates the test fixture 16 in greater detail. The test fixture 16 includes two plates: an upper plate 26 and a lower plate 28. Each plate 26 and 28 includes three load cells 30, 32, and 34 (best seen in FIG. 3). The upper plate is connected to a mechanism such as a linear, geared rack so that it may be moved in a controlled manner up and down along a vertical axis VA. The test fixture 16 also includes a height position device 38 that measures the position of the upper plate 26. In the embodiment shown, the test fixture 16 includes an ACU Right Companies Inc., 10 um Absolute Zero II height measurement device to measure the position of a first base plate 40 on the upper plate 26 with respect to the top surface of a second base plate 50 mounted on the bottom plate 28. As will be described below, load cells 30, 32, and 34 are positioned within recesses in the first base plate 40 (see FIG. 3). A specimen plate 43 is positioned on the base plate 40 and the load cells 30, 32, and 34. The specimen plate 43 includes a circular protrusion or centering mechanism 45 (e.g., a short cylindrical protrusion). The circular protrusion 45 is dimensioned such that the inner circumference of an end ring of a spring to be tested (such as a spring 47) fits snugly around the outer circumference of the circular protrusion 45.

As noted, the bottom plate 28 includes a lower base plate 50. A second specimen plate 51 (having a circular protrusion or centering mechanism 52) is positioned on the lower base plate 50. When a spring is tested in the tester 16, an end ring of a spring (e.g., spring 47) is placed around the protrusion 52 of the second specimen plate 51. Then upper plate 26 is lowered or moved down to compress the spring 47. During compression, load centers at each spring end are recorded by the data logger 20 either continuously or when selected heights (in decreasing size) are reached.

Figure 3:
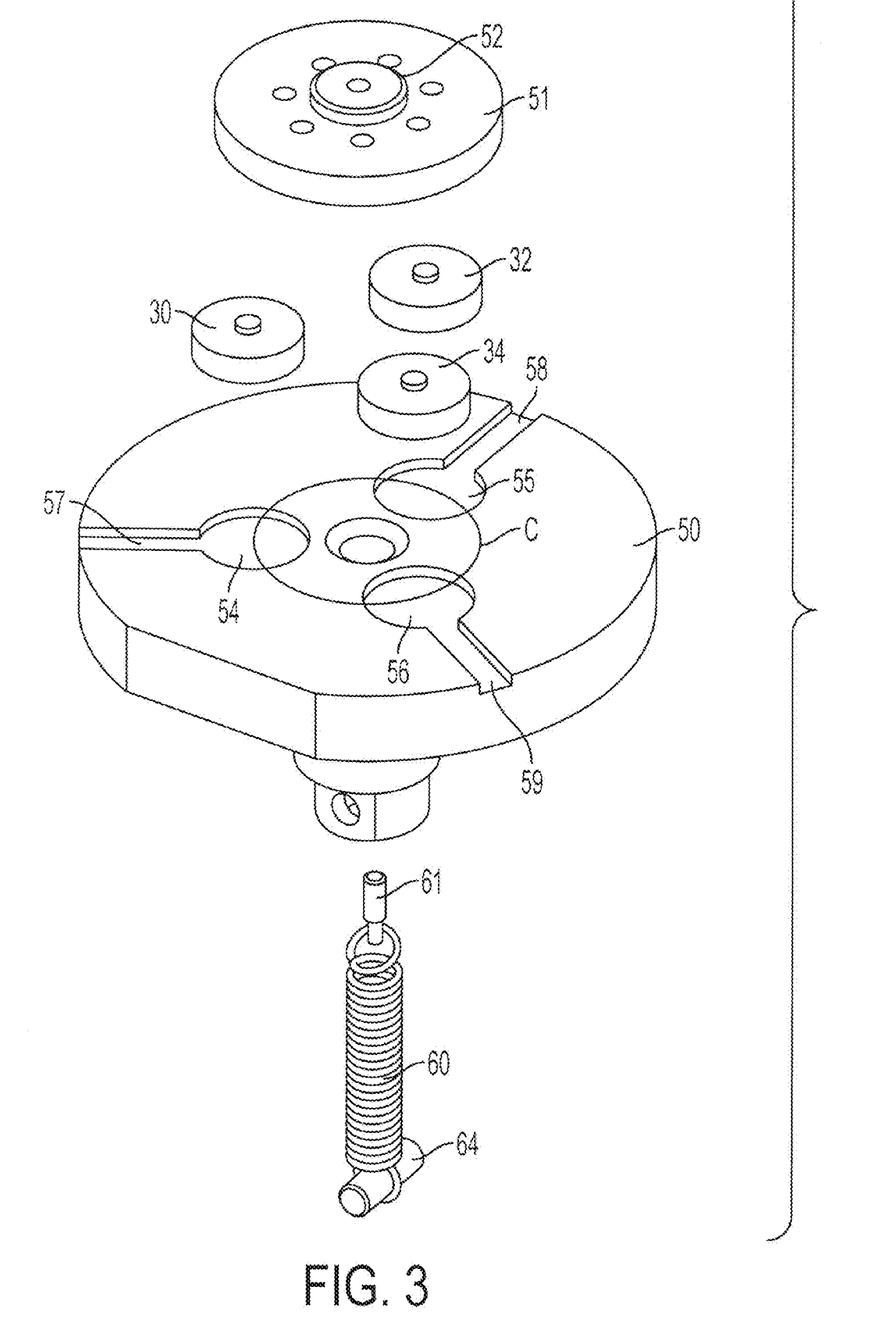
FIG. 3 is an exploded view of a spring testing fixture (or plate and load-cell assembly) used in one embodiment of the invention.

FIG. 3 illustrates an exploded view of components mounted on or otherwise associated with the lower plate 28 (sometimes referred to as a lower fixture). Although only the components related to the lower plate 28 are illustrated, similar components are mounted on or otherwise associated with the upper plate 26. As noted, the base plate 50 is mounted on the lower plate 28. The base plate 50 includes three recesses 54, 55, and 56. The recesses 54, 55, and 56 are positioned and spaced with respect to one another such that the center of each recess is a point on a circle C that is coaxial to the base plate 50. The spacing and positioning of the recesses 54, 55, and 56 is such that the main measurement axes of the load cells can be positioned parallel with respect to one another. Each of the recesses 54, 55, and 56 is sized to receive a single load cell such as one of the load cells 30, 32, and 34. Each recess 54, 55, and 56 also has a guide or channel dimensioned to hold a wire or cable connected to a load cell. In the embodiment shown, the base plate 50 includes three cable channels 57, 58, and 59.

As noted, each load cell generates an output, and the three load cells in the base plate 50 generate three outputs (one each) corresponding to three forces: F1, F2, and F3. The load cells in the base plate 40 of the upper plate 26 generate outputs corresponding to three other forces: F4, F5, and F6.

The known and selected orientation of the load cells 30, 32, and 34 and their outputs provide information used to determine the X-Y position of the load center at each spring end.

Figure 4:
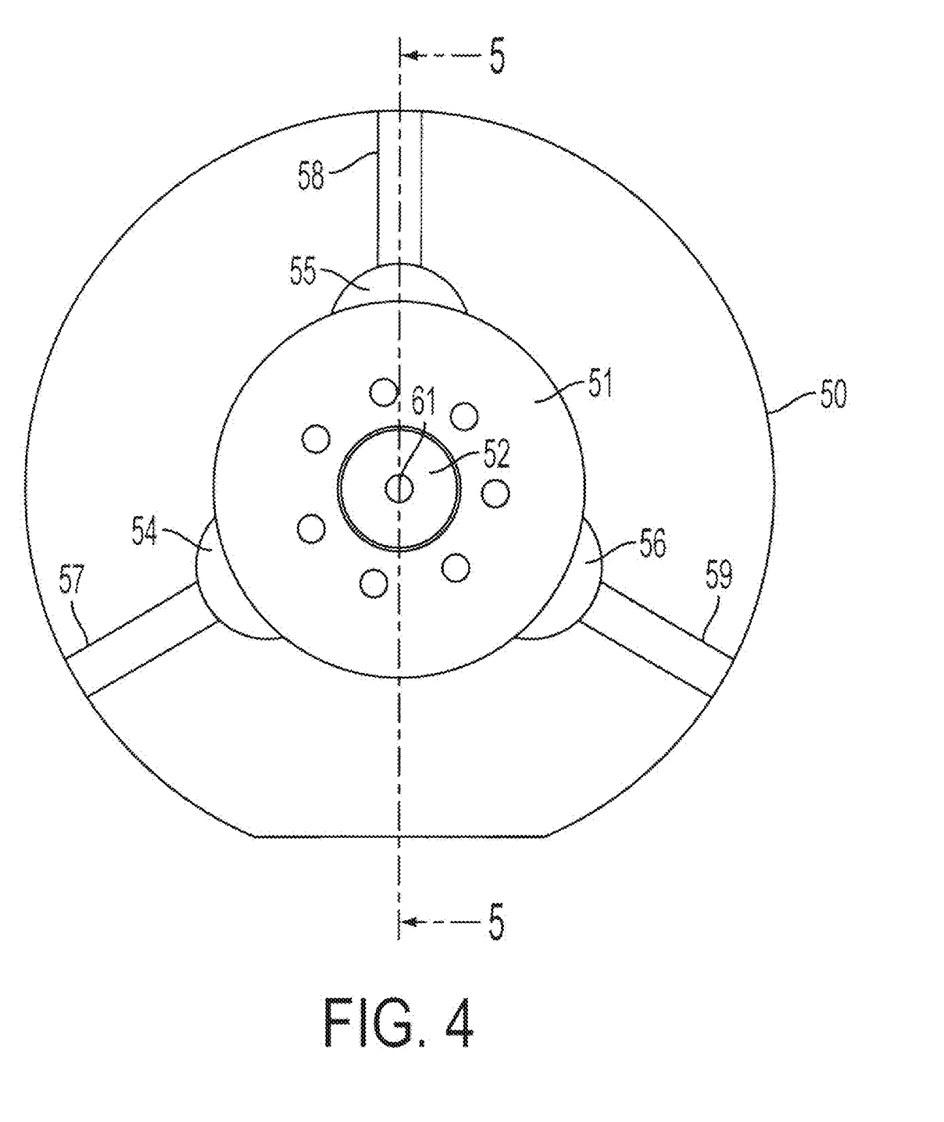
FIG. 4 is an elevation view of the assembled spring test fixture shown in FIG. 3.
Figure 5:
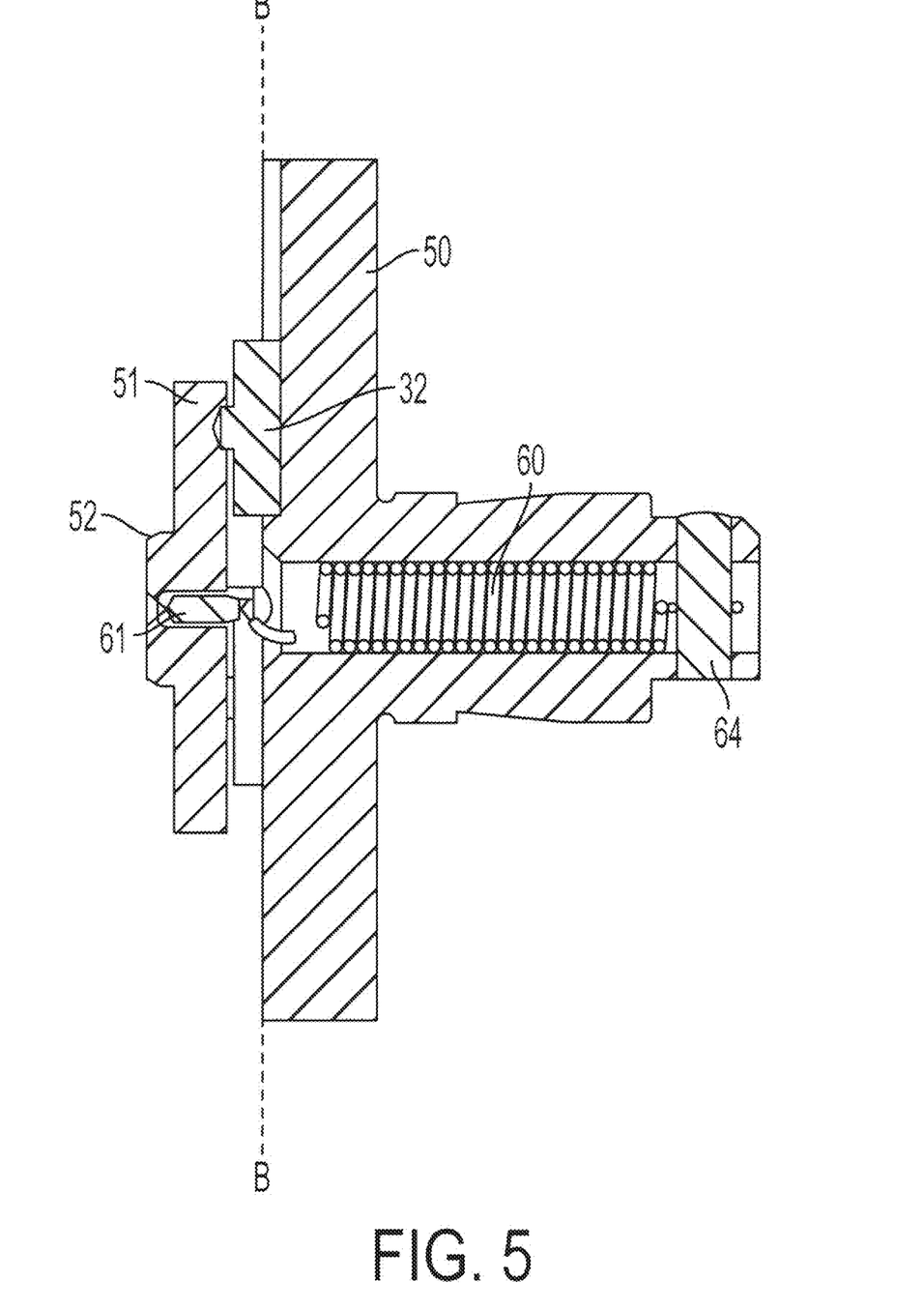
FIG. 5 is a sectional view of the assembled spring test fixture shown in FIGS. 3 and 4.

Each base plate 40, 50 is biased with a tension spring, such as the spring 60 shown in FIG. 3. The spring 60 has a first end with a means, such as a pin 61, for connecting the upper end of the spring 60 to the specimen plate 51. The spring 60 has a second end with a means, such as a dowel pin 64, for connecting the lower end of the spring 60 to the base plate 50. FIG. 4 illustrates a top view of the lower portion of the test fixture 16 showing (beginning with the center and working outwards), the pin 61, the protrusion 52, the specimen plate 51, and the base plate 50. FIG. 5 illustrates a cross-sectional view of the assembly in FIG. 4 taken along line B-B.

Figure 6:
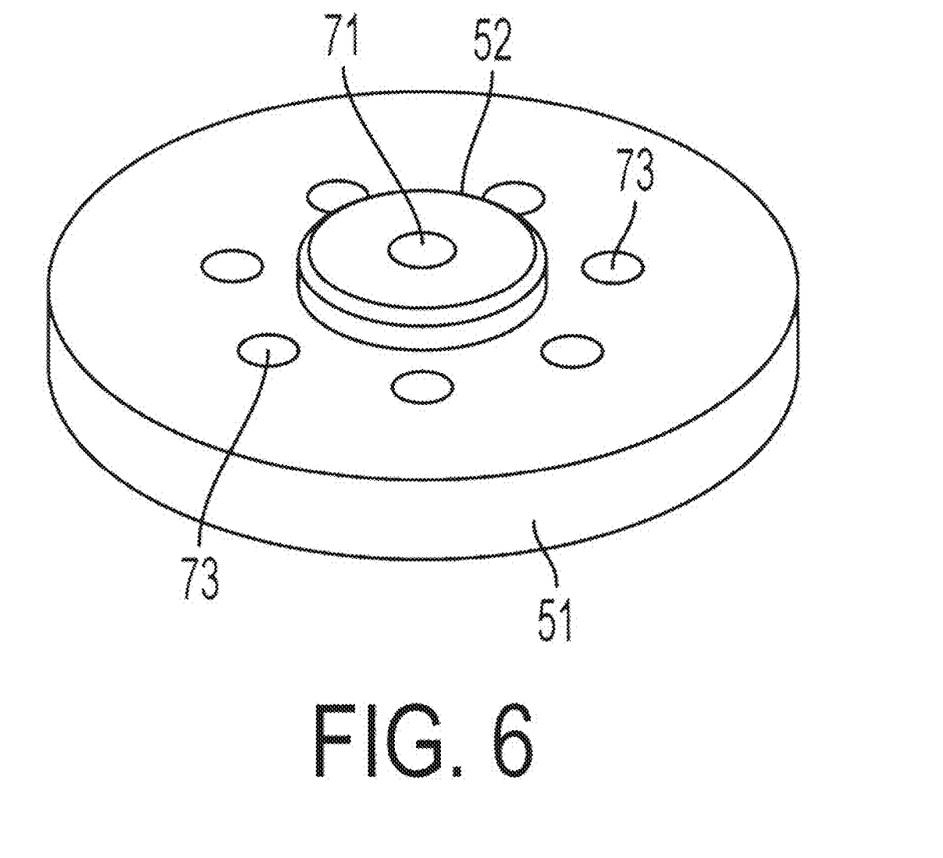
FIG. 6 is a perspective view of a specimen plate of the spring test fixture.

FIG. 6 illustrates the specimen plate 51 in perspective view without other components. As shown, the specimen plate 51 includes a central opening 71 for receiving pin 61 and the centering mechanism 52. Although shown as an integral component, the centering mechanism 52 can be made to be detachable and exchangeable to improve accuracy for spring diameter variation or to accommodate other spring diameter sizes. The specimen plate 51 also includes seven countersink holes 73. The countersink holes 73 are used with a calibration device to verify X-Y load center position accuracy.

Figure 7:
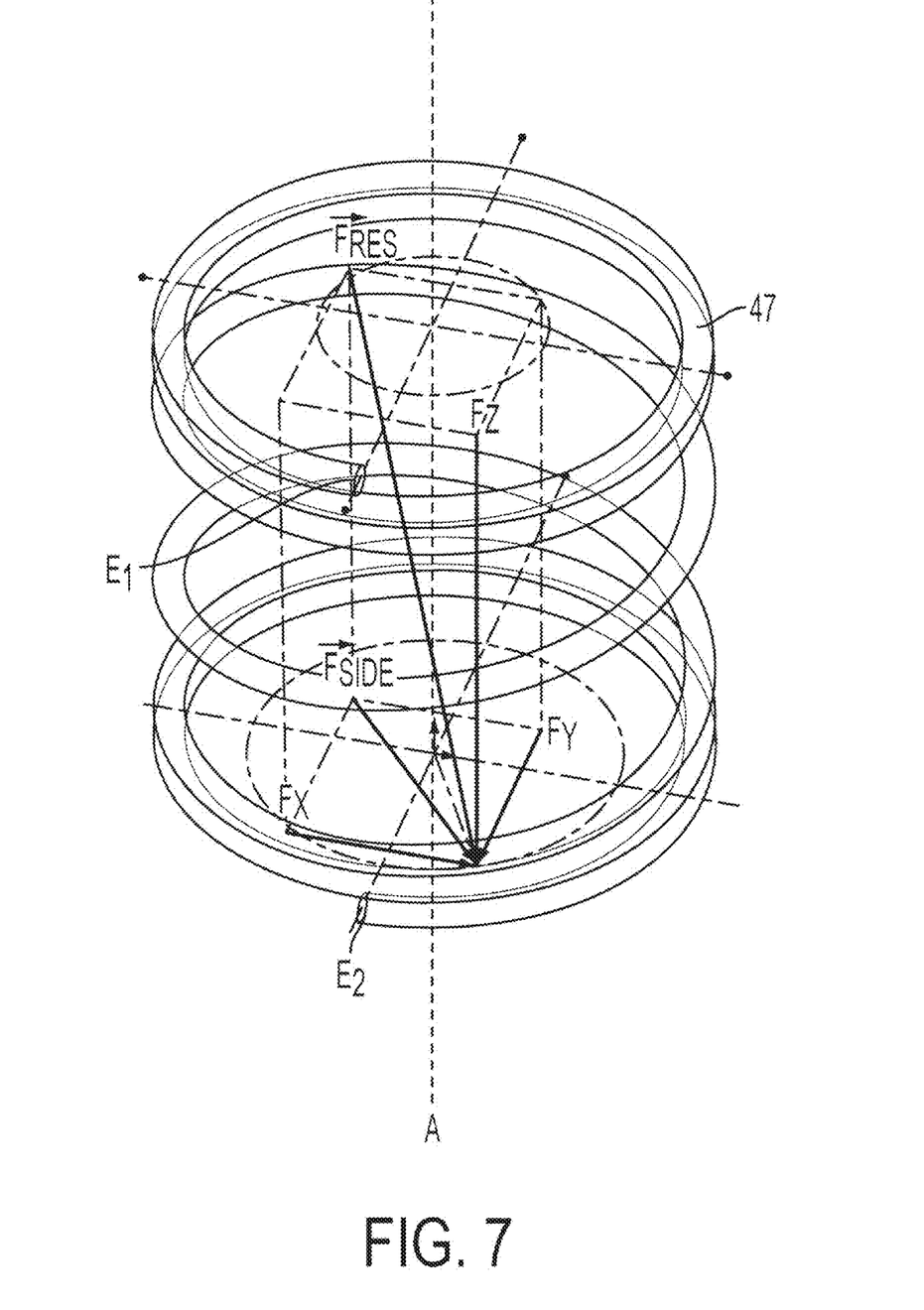
FIG. 7 is a perspective view of a helical spring with force vectors illustrated as applied by the spring tester assembly.
Figure 8:
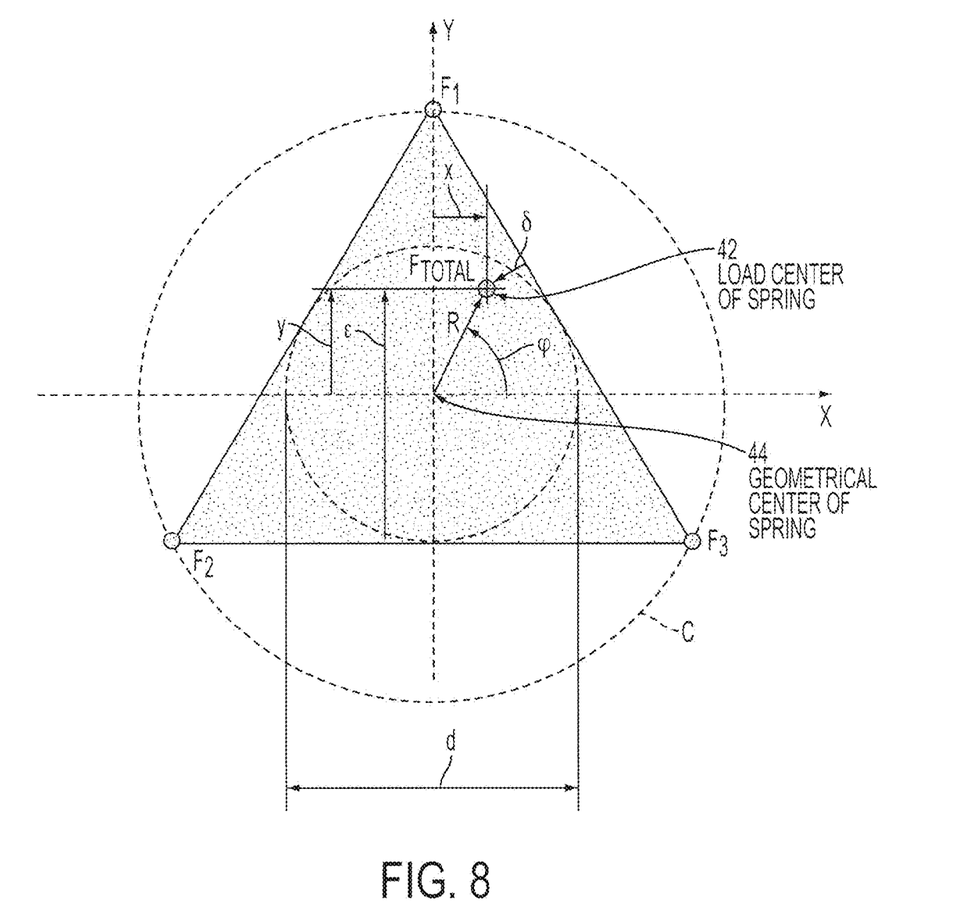
FIG. 8 illustrates the geometrical relationship of three load cells of the spring test fixture.

FIG. 7 illustrates the force vectors applied by the spring tester to a spring such as the spring 47. To determine an X-Y position of the Fres penetration point at each spring end $E_1$ and $E_2$ as well as vectors Fx, Fy, and Fz at any given height or continuously during compression, the data logger 20 stores a data set for each spring end and calibrates the spring tester system 12 for X-Y position and Fz, which is the force acting collinearly to the spring axis A. (A vector penetration point is the point where the resulting spring force vector Fres penetrates the test plane each spring end is resting on.) As shown in FIG. 8, the load cells 26 are positioned in a pattern such that if a line were drawn connecting each load cell application point to each of the two other load cell application points, the three resulting lines would be tangent to a circle coinciding with the spring axis A and having a diameter d bigger than double the expected maximum radius R derived from the load center 42 to the geometrical center 44 of the spring 18.

The data logger 20 stores load cell voltages, and the computer 24 calculates a force based on individual load cell calibration data. For calibration, upper and lower plates 26 and 28 are aligned such that both specimen plates 43 and 51 are parallel and concentric to each other and perpendicular to the moving direction of the upper plate 26 (i.e., perpendicular to the axis VA). This is calibrated with a common coordinate measurement machine (CMM) (not shown), such as, for example, a Browne & Sharpe model Xcel 7.6.5.

X-Y load center position is calibrated by applying a spring-loaded calibration device for two different heights and two forces, which represent the limits of operation. Each calibration device has a precision ground 1 mm ball at each end. Each ball is placed in a counter sink on the upper and lower specimen plates. Each countersink 73 has a known CMM measured X-Y position. In calibration mode, the computer 24 copies the actual X-Y values into memory and applies the obtained values to a compensation algorithm to increase accuracy.

Figure 9:
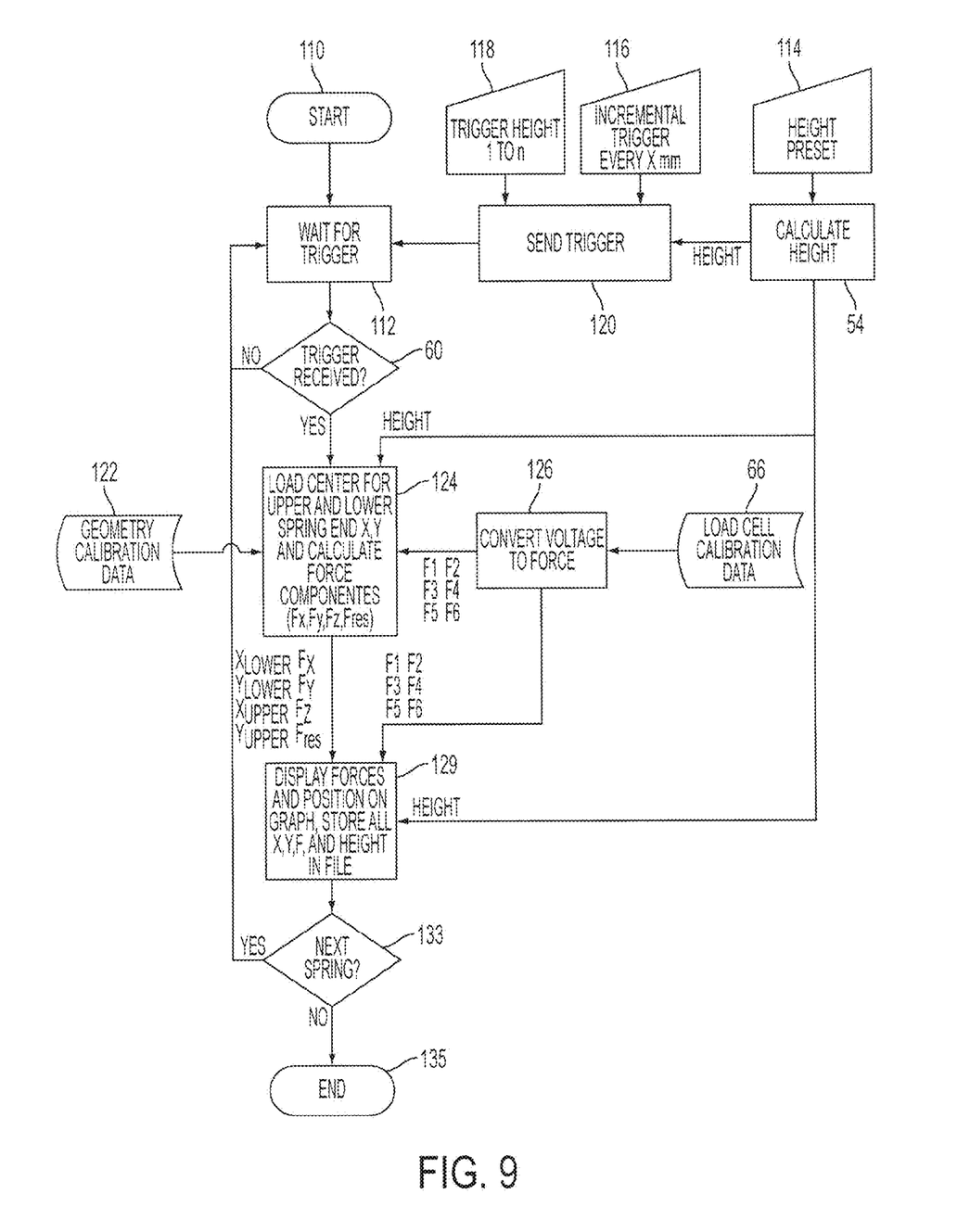
FIG. 9 illustrates, in simplified process flow diagram form, a computerized process of calculating the forces acting on and the position of a spring.

Based on the force distribution on the three load cells 30, 32, and 34, the computer 24 calculates the actual load center of the spring force at the respective ends of a spring, such as the spring 47. The software compensates for geometrical deviations based on actual load cell position and orientation. FIG. 9 illustrates, in simplified process flow diagram form, a computerized process of calculating the forces acting on and the position of a spring. FIG. 9 shows the basic logic of the software as the spring test progresses. The software follows the steps shown in the FIG. 9 and allows the user to automatically analyze the spring forces and position using the spring testing system 12.

From a starting point (block 110) the software waits for a trigger (block 112) to record data. Also, the height position is continuously calculated relative to a preset height (block 114) based on user preference (e.g., 0 mm, 15 mm, etc.) at characteristic positions of the upper plate (26) (e.g., the upper plate touches the lower plate, the upper plate touches a spacer of known height sitting on the lower plate, and the like). If no trigger is received, the system continues to wait. A trigger results in one of two ways. As noted, measurements may be taken as the upper plate 26 is lowered when the height of the plate 26 reached predetermined values. The software then calculates the current height and sends a trigger when even one of the specific trigger heights is measured (block 118). Second, an incremental trigger (block 116) may be set. An incremental trigger is sent at predetermined height intervals (e.g., every two millimeters). If a trigger is received, the software uses geometry calibration data (block 122) and calculates the load center for the upper and lower spring ends, calculates their X-Y positions, and calculates force components Fx, Fy, Fz, and Fres (block 124). In order to correctly calculate these values, load cell calibration data is incorporated, and voltages read from the data logger 20 are converted to force values (block 126). The software then displays forces and position on a graph (block 129), and stores all X-Y coordinates and other data, as well as height where the measurement was taken in a file. If another measurement of the same spring is to be taken, the system waits for another trigger. If a new spring is to be measured (block 133), the software's measurement process returns to block 112. Otherwise, the process ends (block 135).

Figure 10:
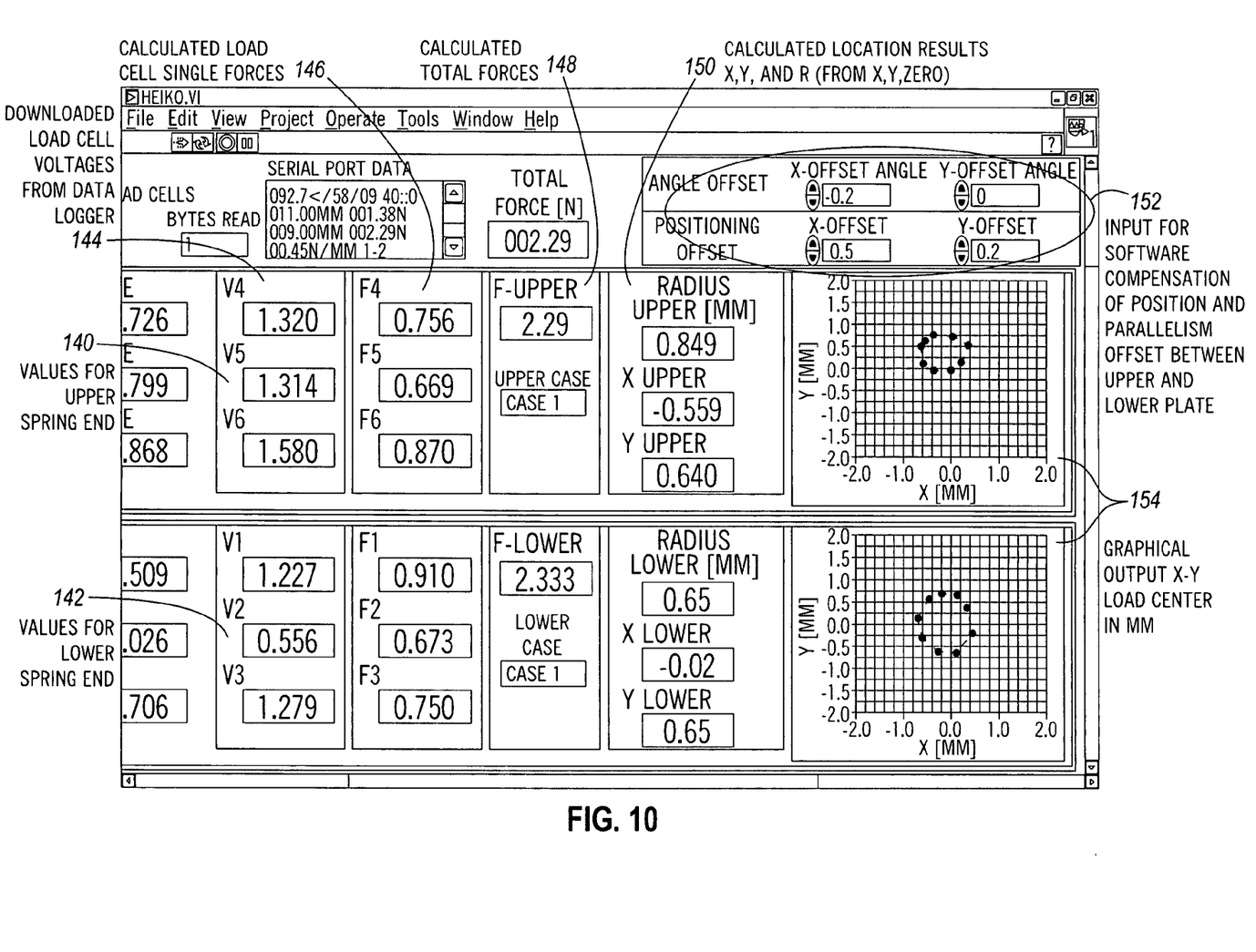
FIG. 10 illustrates a screenshot of a computer software program operating in accordance with one embodiment of the present invention.

FIG. 10 shows a sample screenshot of software data output in one embodiment. The software output displays the measured and calculated data. In one embodiment, the software output display includes values 140 for the upper end of a spring, values 142 for the lower end of a spring, downloaded load cell voltages 144 from the data logger 20, calculated load cell single force components 146, calculated total forces 148, calculated location results 150, input 152 for software compensation of position and parallelism offset between the upper and lower plate 26 and 28, and graphical output 154 of the X-Y load center.

Embodiments of the invention determine a load distribution on each end of a spring with a cylindrical shape using three mutually parallel load cells. The spring force tester system has the capability of measuring penetration points (at both spring ends) of spring force vectors Fx, Fy, Fz, and Fres of helical springs, wave springs, disc springs, and other types of springs with generally cylindrical shape and is designed to measure forces ranging from low primary forces as small as 0.5N up to forces of 100N acting along the spring axis A. Force components that are collinear with the spring axis A can be measured and calculated into vector penetration point coordinates.

The spring force tester system 16 can determine side forces and moments in a primary direction and in other directions, and it can operate at total spring forces as low as 0.5N.

Having described certain embodiments of the invention with reference to the accompanying drawings, it is to be understood that the invention is not limited to those precise embodiments, and that various changes and modifications may be effected therein by one skilled in the art without departing from the scope or spirit of the invention as defined in the appended claims. A number of modifications may be made to the present invention without departing from the inventive concept therein. Modifications to the preferred embodiment may be made within the scope of the present invention.

What is claimed is:

1. A system for testing a spring, the system comprising:
   a lower plate including a plurality of recesses and a load cell positioned in each of the plurality of recesses, the plurality of recesses positioned such that a center of each recess is a point on a circle coaxial to the lower plate;
   an upper plate movable with respect to the lower plate and including a plurality of recesses and a load cell positioned in each of the plurality of recesses, the plurality of recesses positioned such that a center of each recess is a point on a circle coaxial to the upper plate;
   a data logger that obtains and stores load cell outputs from the load cells in the lower plate and the upper plate;
   spring tester electronics that obtain height measurements of the upper plate and send a trigger signal to a computer; and
   the computer including a processor and a memory module, the memory module storing application software executable by the processor when the computer receives the trigger signal to:
   read the load cell outputs stored in the data logger, and calculate a spring force based on the load cell outputs, wherein the spring force is between approximately 0.5 Newton and 100 Newton.

2. The system of claim 1, wherein the circle, along which the center of each recess included in the lower plate is positioned, has a diameter bigger than twice an expected maximum radius, the expected maximum radius derived from a load center of the spring and a geometrical center of the spring.

3. The system of claim 1, wherein the circle, along which the center of each recess included in the upper plate is positioned, has a diameter bigger than twice an expected maximum radius, the expected maximum radius derived from a load center of the spring and a geometrical center of the spring.

4. The system of claim 1, wherein each recess included in the lower plate is positioned equidistant around the circle.

5. The system of claim 1, wherein each recess included in the upper plate is positioned equidistant around the circle.

6. The system of claim 1, further comprising a height position device that measures the position of the upper plate and transmits the height measurements of the upper plate to the spring tester electronics.

7. The system of claim 1, wherein the spring tester electronics sends the trigger signal to the computer when the height measurements indicate that the upper plate is at a predetermined height.

8. The system of claim 1, wherein the application software executable by the processor of the computer outputs the spring force.

9. The system of claim 8, wherein the application software executable by the processor of the computer outputs the spring force in at least one of a spreadsheet and an ASCII file.

10. A method of calibrating a spring tester device comprising:
    providing a lower plate including a plurality of recesses and a load cell positioned in each of the plurality of recesses, the plurality of recesses positioned such that a center of each recess is a point on a circle coaxial to the lower plate;
    providing an upper plate movable with respect to the lower plate and including a plurality of recesses and a load cell positioned in each of the plurality of recesses, the plurality of recesses positioned such that a center of each recess is a point on a circle coaxial to the upper plate;
    providing a first specimen plate positioned on the lower plate and including a plurality of countersinks;
    providing a second specimen plate positioned on the upper plate and including a plurality of countersinks;
    aligning the lower plate and the upper plate such that the first specimen plate is parallel and concentric with the second specimen plate;
    positioning a spring-loaded calibration device perpendicular and between the first specimen plate and the second specimen plate by positioning a first end of the calibration device in one of the plurality of countersinks in the first specimen plate and positioning a second end of the calibration device in one of the plurality of countersinks in the second specimen plate;
    calculating a spring force of the spring-loaded calibration device based on load cell outputs generated by the load cells included in the lower plate and the upper plate, wherein the spring force is between approximately 0.5 Newton and 100 Newton; and
    using the calculated spring force, a known spring force for the spring-loaded calibration device, and positions of the plurality of countersinks in the first specimen plate and the second specimen plate to calibrate the spring tester device.

11. The method of claim 10, wherein providing a lower plate including a plurality of recesses and a load cell positioned in each of the plurality of recesses includes providing a lower plate wherein the circle has a diameter bigger than twice an expected maximum radius, the expected maximum radius derived from a load center of the spring and a geometrical center of the spring.

12. The method of claim 10, wherein providing an upper plate including a plurality of recesses and a load cell positioned in each of the plurality of recesses includes providing an upper plate wherein the circle has a diameter bigger than twice an expected maximum radius, the expected maximum radius derived from a load center of the spring and a geometrical center of the spring.

13. The method of claim 10, wherein providing a lower plate including a plurality of recesses and a load cell positioned in each of the plurality of recesses includes providing a lower plate wherein each of the plurality of recesses is positioned equidistant around the circle.

14. The method of claim 10, wherein providing an upper plate including a plurality of recesses and a load cell positioned in each of the plurality of recesses includes providing an upper plate wherein each of the plurality of recesses is positioned equidistant around the circle.

15. The method of claim 10, further comprising a ball in the first end and the second end of the calibration device.

16. The method of claim 10, wherein positioning the spring-loaded calibration device between the first specimen plate and the second specimen plate includes positioning the spring-loaded calibration device between the first specimen plate and the second specimen plate when the first specimen plate and the second specimen plate are separated by a first predetermined distance and when the first specimen plate and the second specimen plate are separated by a second predetermined distance.

17. The method of claim 10, wherein positioning the spring-loaded calibration device between the first specimen plate and the second specimen plate includes positioning the spring-loaded calibration device set to a first predetermined spring force between the first specimen plate and the second specimen plate and positioning the spring-loaded calibration device set to a second predetermined spring force between the first specimen plate and the second specimen plate.

18. The method of claim 17, wherein the first predetermined spring force is approximately 0.5 Newton and the second predetermined spring force is approximately 100 Newton.

19. The method of claim 10, wherein aligning the lower plate and the upper plate includes using a common coordinate measurement machine to align the lower plate and the upper plate such that the first specimen plate is parallel and concentric with the second specimen plate.

20. A method of inspecting a spring comprising:
providing a lower plate including a plurality of recesses and a load cell positioned in each of the plurality of recesses, the plurality of recesses positioned such that a center of each recess is a point on a circle coaxial to the lower plate;
providing an upper plate movable with respect to the lower plate and including a plurality of recesses and a load cell positioned in each of the plurality of recesses, the plurality of recesses positioned such that a center of each recess is a point on a circle coaxial to the upper plate;
positioning the spring perpendicular to and between the lower plate and the upper plate;
determining a height of the upper plate;
obtaining load cell outputs from the load cells positioned in the lower plate and the upper plate; and
calculating a load center for a first end of the spring and a load center for a second end of the spring based on the load cell outputs.

21. The method of claim 20, further comprising outputting the load center for the first end of the spring and the load center for the second end of the spring to a display.

22. The method of claim 20, wherein providing a lower plate including a plurality of recesses and a load cell positioned in each of the plurality of recesses includes providing a lower plate wherein the circle has a diameter bigger than twice an expected maximum radius, the expected maximum radius derived from a load center of the spring and a geometrical center of the spring.

23. The method of claim 20, wherein providing an upper plate including a plurality of recesses and a load cell positioned in each of the plurality of recesses includes providing an upper plate wherein the circle has a diameter bigger than twice an expected maximum radius, the expected maximum radius derived from a load center of the spring and a geometrical center of the spring.

24. The method of claim 20, wherein providing a lower plate including a plurality of recesses and a load cell positioned in each of the plurality of recesses includes providing a lower plate wherein each of the plurality of recesses is positioned equidistant around the circle.

25. The method of claim 20, wherein providing an upper plate including a plurality of recesses and a load cell positioned in each of the plurality of recesses includes providing an upper plate wherein each of the plurality of recesses is positioned equidistant around the circle.

26. The method of claim 20, further comprising calculating force components collinear with an axis of the spring, vector penetration point coordinates based on the calculated force components collinear with the axis of the spring, a resulting force vector based on the vector penetration points, force components not collinear with the axis of the spring based on the vector penetration points, and related moments of the spring based on the vector penetration points.

27. The method of claim 26, further comprising outputting the force components collinear with an axis of the spring, the vector penetration point coordinates, the resulting force vector, the force components not collinear with the axis of the spring, and the related moments of the spring to the display.

* * * * *